(12) United States Patent
Carman et al.

(10) Patent No.: US 7,466,403 B2
(45) Date of Patent: Dec. 16, 2008

(54) GRAIN ANGLE SENSOR

(75) Inventors: George M. Carman, Corvallis, OR (US); William J. Briskey, Monmouth, OR (US); David D. Ayers, Salem, OR (US); David K. Christopher, Lebanon, OR (US); Patrick S. Freeman, Corvallis, OR (US); Chad D. Gibson, Corvallis, OR (US); Aaron R. Paul, Corvallis, OR (US); Paul Shirkey, Corvallis, OR (US); Joseph H. Weintraub, Elkins Park, PA (US)

(73) Assignee: Lucidyne Technologies, Inc., Corvallis, OR (US)

( * ) Notice: Subject to any disclaimer, the term of this patent is extended or adjusted under 35 U.S.C. 154(b) by 0 days.

(21) Appl. No.: 11/858,708

(22) Filed: Sep. 20, 2007

(65) Prior Publication Data

US 2008/0074670 A1  Mar. 27, 2008

Related U.S. Application Data

(60) Provisional application No. 60/826,365, filed on Sep. 20, 2006.

(51) Int. Cl.
*G01N 21/00* (2006.01)
(52) U.S. Cl. .................................. 356/237.2; 356/446
(58) Field of Classification Search ... 356/237.1–237.5, 356/445–448, 369; 250/559.25; 382/108–111, 382/141–143; 702/33–36, 150–151
See application file for complete search history.

(56) References Cited

U.S. PATENT DOCUMENTS

| | | | |
|---|---|---|---|
| 4,086,496 A | 4/1978 | Berry | |
| 4,207,472 A | 6/1980 | Idelsohn et al. | |
| 4,221,974 A | 9/1980 | Mueller et al. | |
| 4,286,880 A | 9/1981 | Young | |
| 4,301,373 A | 11/1981 | Sjödin | |
| 4,606,645 A | 8/1986 | Matthews et al. | |
| 4,738,533 A | 4/1988 | Iwamoto | |
| 4,827,142 A | 5/1989 | Hatje | |
| 4,831,545 A | 5/1989 | Floyd et al. | |
| 4,867,213 A | 9/1989 | Bolton et al. | |
| 4,879,752 A | 11/1989 | Aune et al. | |
| 4,916,629 A | 4/1990 | Bogue et al. | |
| 4,926,350 A | 5/1990 | Bechtel et al. | |
| 4,992,949 A | 2/1991 | Arden | |

(Continued)

OTHER PUBLICATIONS

LuxScan Front End Scanner FES 150 Brochure (Sep. 7, 2004) with (Feb. 6, 2008) version.

(Continued)

*Primary Examiner*—Hoa Q Pham
(74) *Attorney, Agent, or Firm*—Stoel Rives LLP

(57) ABSTRACT

A grain angle sensor system for measuring grain angle direction of surface fibers of a wood object with respect to at least one of a surface plane direction or a transverse direction, such as a dive angle, or with respect to both the surface plane and transverse direction. The system includes multiple laser diodes and photosensor detectors integrated into an electro-optical assembly that can sequence the firing of the lasers to minimize crosstalk. An exemplary assembly includes an enclosure housing an electronic control board connected to circuit cards containing multiple laser diodes and multiple photosensor detectors.

33 Claims, 5 Drawing Sheets

U.S. PATENT DOCUMENTS

| | | | |
|---|---|---|---|
| 5,252,836 A | 10/1993 | Matthews et al. | |
| 5,254,859 A | 10/1993 | Carman et al. | |
| 5,412,220 A | 5/1995 | Moore | |
| 5,421,385 A | 6/1995 | McGee | |
| 5,524,771 A | 6/1996 | Kairi et al. | |
| 5,544,757 A | 8/1996 | Geiger et al. | |
| 5,644,392 A | 7/1997 | Soest et al. | |
| 5,703,960 A | 12/1997 | Soest | |
| 5,960,104 A | 9/1999 | Conners et al. | |
| 6,272,437 B1 | 8/2001 | Woods et al. | |
| 6,624,883 B1 * | 9/2003 | Zhou et al. | 356/237.1 |
| 6,756,789 B1 | 6/2004 | Parker et al. | |
| 6,757,058 B1 | 6/2004 | Carman et al. | |
| 6,813,927 B1 | 11/2004 | Harris et al. | |
| 7,004,329 B2 | 2/2006 | Magnan | |
| 7,200,458 B2 | 4/2007 | Carman et al. | |
| 2002/0025061 A1 | 2/2002 | Metcalfe et al. | |
| 2003/0079544 A1 | 5/2003 | Floyd | |
| 2003/0192412 A1 | 10/2003 | Otto et al. | |

OTHER PUBLICATIONS

Richard W. Conners, D. Earl Kline, Philip A. Araman, and Thomas H. Drayer, *IEEE* (Jul. 1997), 43-48, "Machine Vision Technology for the Forest Products Industry".

* cited by examiner

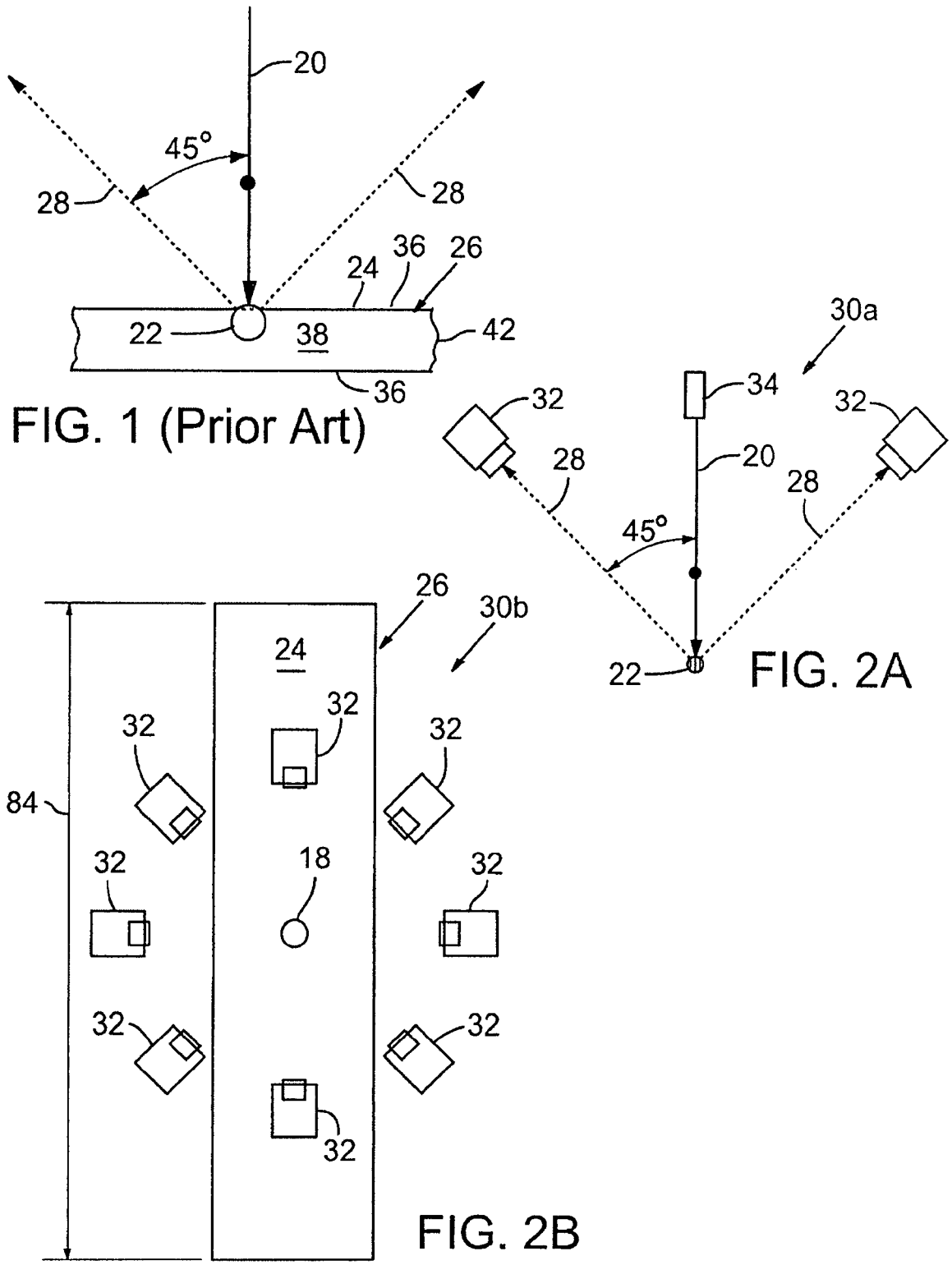

GRAIN ANGLE SENSOR

RELATED APPLICATIONS

This patent application derives priority from U.S. Prov. Pat. Appl. No. 60/826,365, filed Sep. 20, 2006.

TECHNICAL FIELD

The present invention relates generally to tracheid cell direction sensing and, in particular, to a grain angle sensor for measuring grain angle direction of surface fibers of a wood object with respect to at least one of a surface plane direction or a transverse direction, such as a dive angle, or with respect to both the surface plane and transverse direction.

BACKGROUND

The specular reflection properties of a tracheid cell of a wood object are well known. The primary response of light energy 20 striking a tracheid cell 22 on a surface 24 of a wood object 26 can be expressed by a simplified reflection 28 as shown in FIG. 1 The largest quantity of reflected energy is observed at a 45 degree angle with respect to the angle of incidence, and 90 degrees from the direction of the long axis of the tracheid cell 22 when there is no dive angle. A dive angle is present when the tracheid cells 22 align in a direction not parallel with the plane of the surface 24 of the wood object 26. A dive angle can be detected because the direction of the reflected energy varies with the angle of incidence. A detailed discussion concerning the specular and diffuse reflective properties of a wood grain surface can be found in U.S. Pat. No. 4,606,645 of Matthews et al.

Conventional tracheid cell direction sensors 30a and 30b as shown respectively in FIGS. 2A and 2B employ various photosensor devices 32 that detect different reflections of light energy 20, from a light source 34 such as a laser, striking a wood surface 24 with a spot 18. An exemplary tracheid cell direction sensor is described in U.S. Pat. No. 5,252,836 of Matthews et al. Other methods include sweeping a light spot across the surface of a wood object.

One problem with conventional tracheid cell direction sensors is that they are not able to collect sufficient information across the surface 24 of a wood object 26 to satisfy some basic lumber grading requirements, nor are they fast enough at collecting data to perform applications that require real-time data acquisition and decision making. Another problem with conventional tracheid cell direction sensors is that the surface data they collect is not inherently or readily combinable with other location-sensitive data being taken across the face of a wood object 26 because conventional tracheid sensors collect data from a small surface coverage area limited to one spot per surface at any given time.

Another problem with conventional tracheid cell direction sensors is that the physical space required for the detection device is large, creating implementation difficulties in a production application where space is at a premium.

SUMMARY OF THE INVENTION

An object of the present invention is, therefore, to provide an improved grain angle sensor system or method for measuring the direction and dive angle of the surface fiber of wood, or both a sensor system and such method.

One preferred embodiment employs multiple laser diodes and photosensor devices that may be integrated into a single electro-optical assembly. An exemplary assembly may include an enclosure housing an electronic control board connected to circuit cards containing multiple laser diodes and multiple photosensor devices.

Some exemplary embodiments of such a grain angle sensor system or method acquire sufficient data across the surface of a wood object to pattern the surface grain direction for lumber grading, quality, use (or "best use") determinations or decisions.

Some exemplary embodiments of such a grain angle sensor system or method acquire sufficient data fast enough to meet production speed requirements in real-time lumber grading, quality, use (or "best use") determinations or decisions.

Some exemplary embodiments of such a grain angle sensor system or method provide position-referenced data in both width and longitudinal directions to pattern the surface grain direction for lumber grading, quality, use (or "best use") determinations or decisions.

Additional objects and advantages of the present invention will be apparent from the following detailed description of preferred embodiments thereof, which proceeds with reference to the accompanying drawings.

BRIEF DESCRIPTION OF THE DRAWINGS

FIG. 1 is a simplified side view of light impinging a wood surface that demonstrates the basic specular reflectance properties of tracheid cells of wood.

FIGS. 2A and 2B are respective side and top views of exemplary existing methods of grain detection that employ a single light source, such as a laser, and multiple sensors, such as cameras.

DETAILED DESCRIPTION OF PREFERRED EMBODIMENTS

Figure 3:
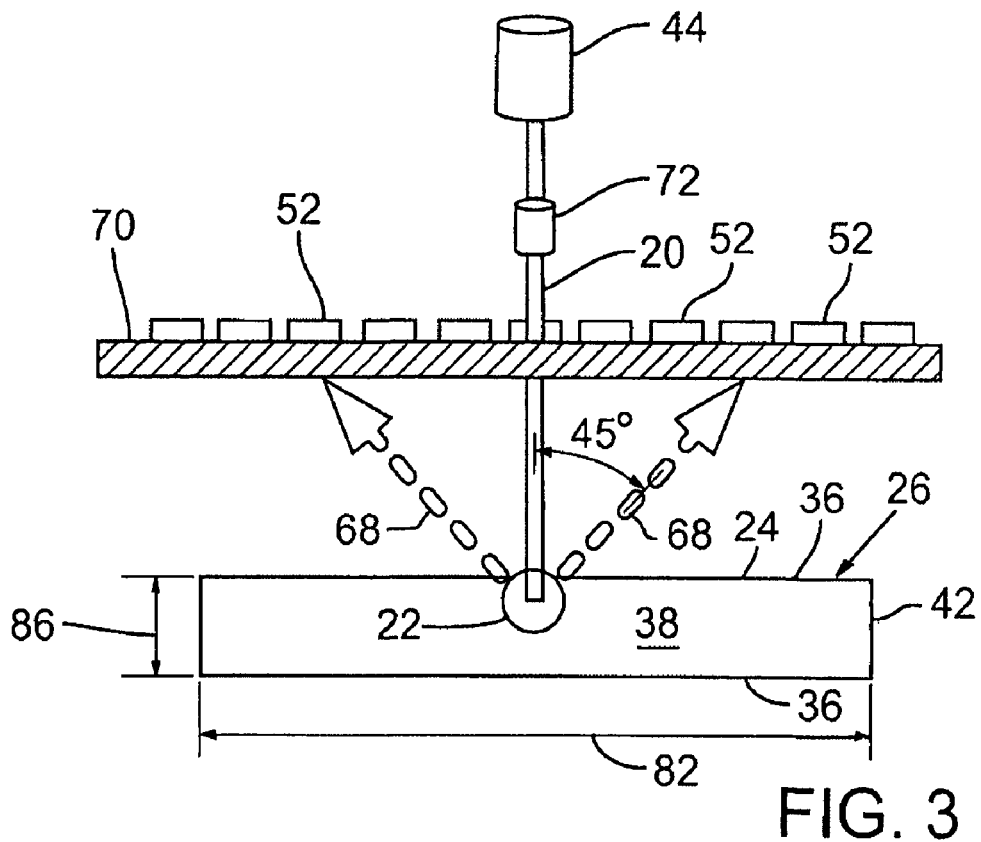
FIG. 3 is a front view of an exemplary functional unit of an improved grain angle detector, the functional unit employing a laser and multiple photosensor detectors.
Figure 4:
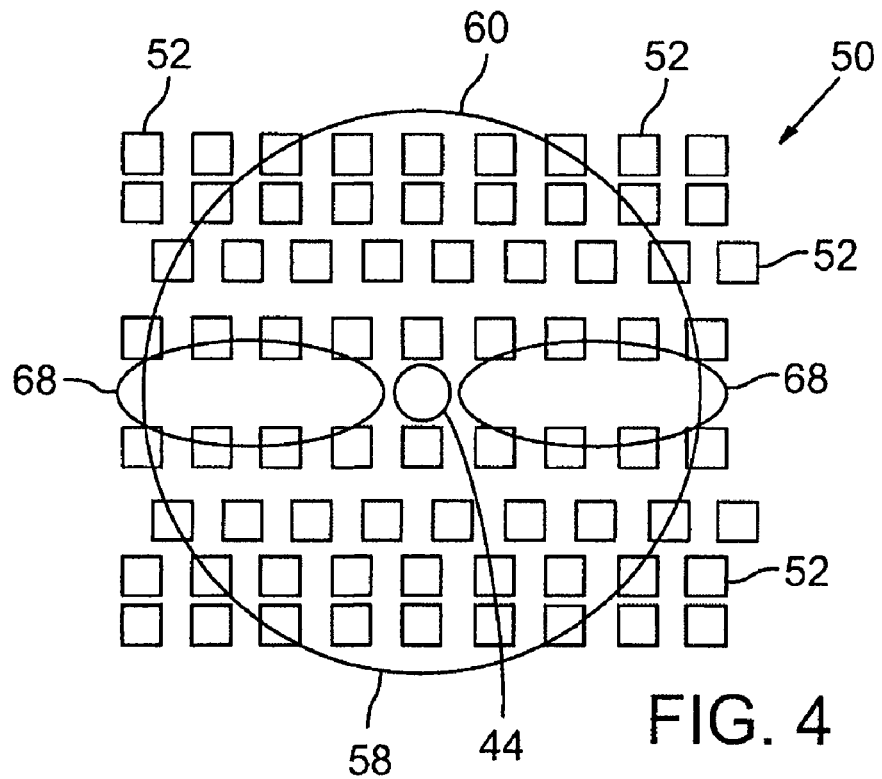
FIG. 4 is a top view of the functional unit shown in FIG. 3.

FIG. 3 and FIG. 4 are respective front and plan views of an exemplary functional unit 50 of a grain angle detection system 40 for illuminating a surface of a wood object 26 and for determining the direction of light energy 68 reflected from the tracheid cells 22 of the wood object 26. For convenience, the terms "wood" or "wood object" 26 may refer to any cut piece of timber, lumber, logs that has an exposed tracheid cell. These pieces may include, but are not limited to, flitches, cants, beams, posts, studs, boards, veneer, and/or any other pieces of wood smaller than the whole tree and larger than sawdust. The surfaces inspected may be one or more faces 36, sides 38, and/or ends 42 of the wood object 26.

With reference to FIGS. 3 and 4, the functional unit 50 employs a light source, such as a laser 44, and a group 60 of photosensor devices 52 that may be positioned within a detection field 58 that may, for example, be positioned within a concentric circle about the laser 44. The detection field 58 is preferably large enough for the group 60 of the photosensor devices 52 to determine the direction of light energy 68 reflected from a target of laser impingement, such as a tracheid cell 22 of a wood object 26. The size of the detection field 58 may be large enough to sense most or all of the reflected light energy 68 or may be reduced to an area that is just large enough for the photosensor devices 52 to make the determination of the direction of the light energy reflected from the target. In some embodiments, the photosensor devices 52 are mounted as dense as their packaging will allow. The laser type and the laser parameters, including at least one of the laser energy, wavelength, spot size, and distance of the laser from the target, as well as the packaging density of the photosensor devices 52 and their distances from the target, may be factors in the determination of a minimum area of field 58 that would be sufficient for determining the direction of the reflected light energy 68. In one exemplary embodiment, sixteen photosensor devices 52 are associated with every laser 44.

In some embodiments, the photosensor devices 52 are mounted in the same plane and "look" through an optically clear plate 70, such as a glass plate. In some embodiments, the photosensor devices 52 can be mounted in different planes. Lenses (not shown) may be optionally employed with some or all of the photosensor devices 52, or the plate 70 may itself have focusing, expanding, or other types of optical properties. In some embodiments, the photosensor devices 52 are supported from a support structure above them and need not "look" through a (glass) support plate. The electronics controlling the photosensor devices 52 enables all their information to be individually captured and recorded. Skilled persons will appreciate, however, that information from all the photosensors within a detection field 58 for a given functional unit 50 may be processed together. The information from the photosensor devices 52 is collected and processed to identify the direction and dive angle (if any) of any tracheid cell 22 impinged by the output of laser 44. The direction and dive angle information can then be used for grading the wood object 26 and determining how the portion of the wood object 26 including the tracheid fiber should be used.

In some embodiments, the laser 44 may be a diode laser or a fiber laser, and it may be mounted in the same plane as, or a different plane than, that of the photosensor devices 52. The laser 44 may be positioned between the rows and/or columns of the photosensor devices 52 and provide laser output that is perpendicular to the surface of the wood object 26. In some embodiments, the output of the laser 44 impinges the surface of the wood object 26 at a nonperpendicular transverse angle. One or more optional optical components 72, such as one or more lenses, may be associated with the laser 44, such as to control its spot size or other optical properties. Alternatively or additionally, the output of the laser 44 may be directed through an optical fiber. The laser output power can additionally or alternatively be adjusted by control electronics (not shown) well known to skilled practitioners.

Figure 5:
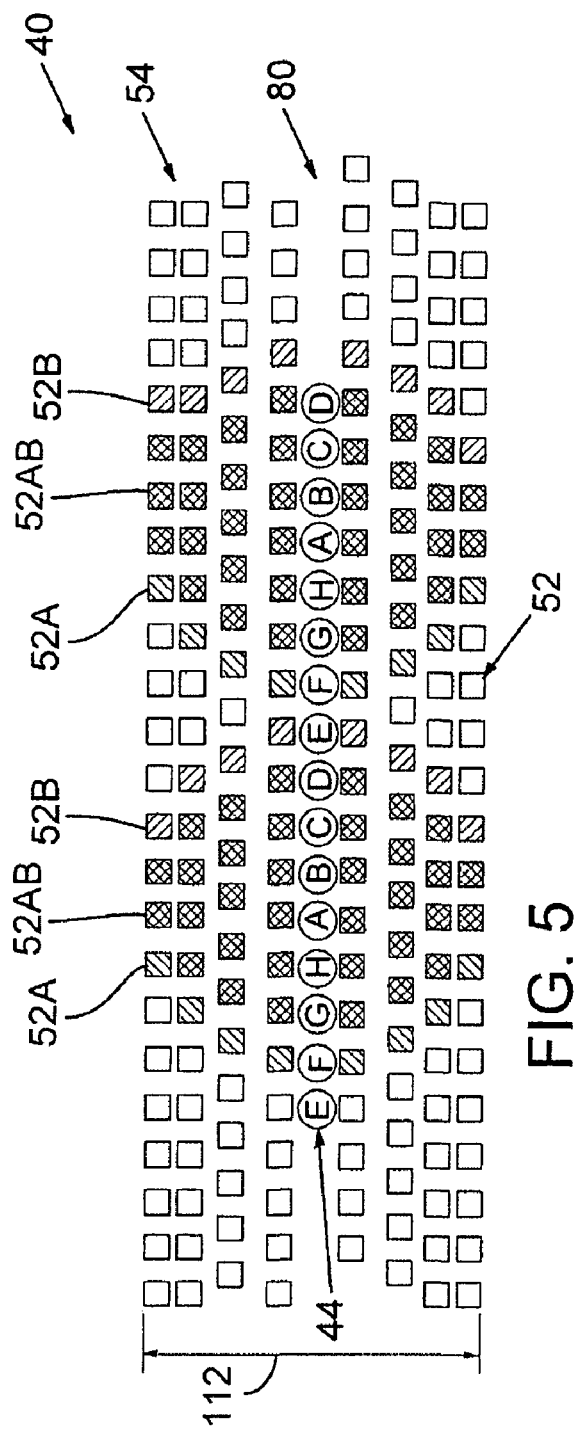
FIG. 5 is a top view of an exemplary improved grain angle detector employing multiple lasers and multiple photosensor detectors.
Figure 6:
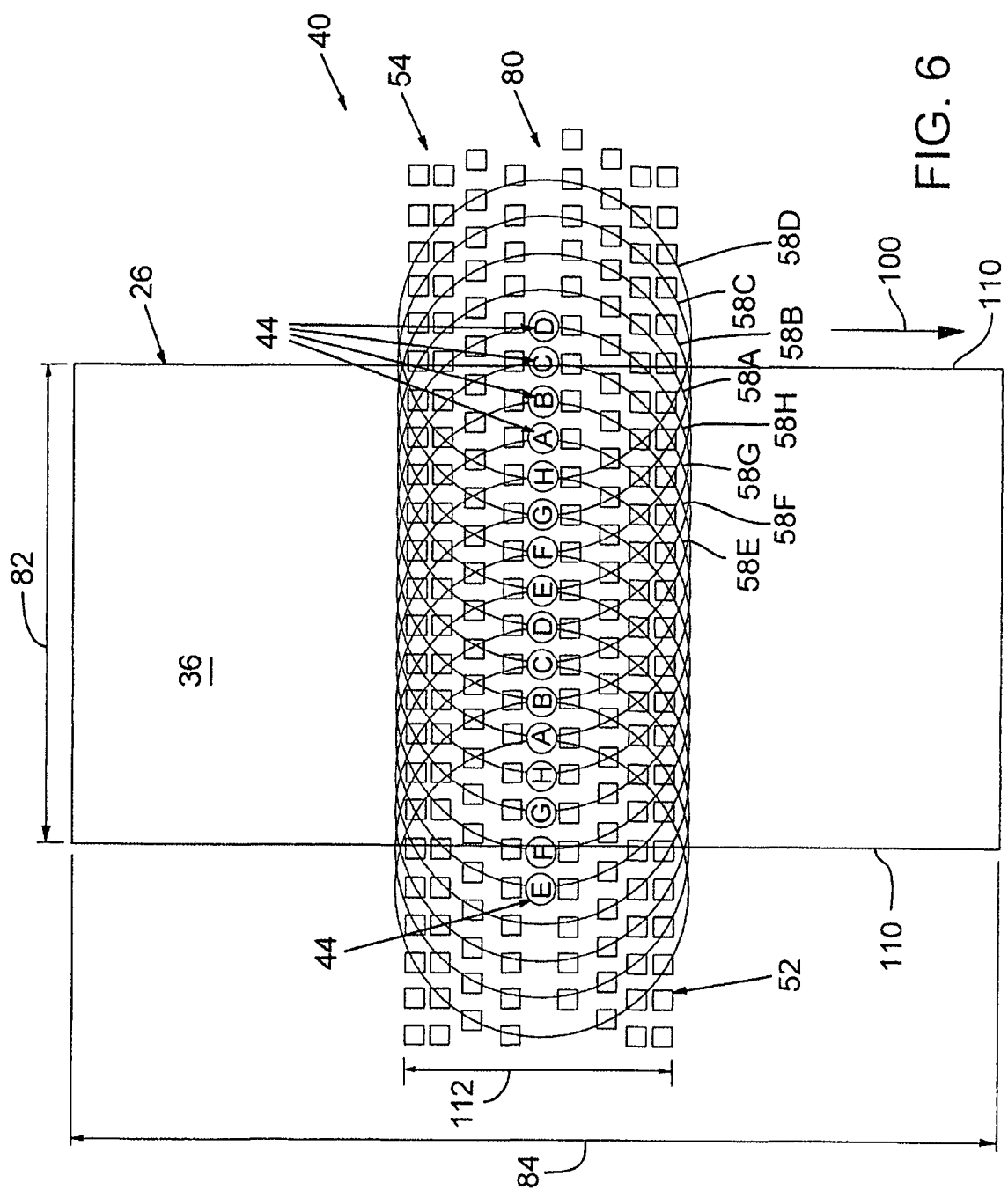
FIG. 6 is a top view of an exemplary improved grain angle detector, demonstrating exemplary overlapping areas of reflected laser energy.

FIG. 5 is a top view showing the arrangement of multiple functional units 50 that form an exemplary detection array unit 54 of an exemplary grain angle detection system 40 employing multiple lasers and multiple photosensor detectors, and FIG. 6 is a top view of the grain angle detection system 40 that emphasizes the exemplary overlapping detection fields 58 (and the photosensor devices 52 they contain) associated with the lasers 44 of the respective functional units 50. With reference to FIGS. 3-6, an exemplary grain angle detection system 40 employs one or more groups or rows 80 (and columns, if desirable) of light sources or lasers 44 that may span an entire dimension of the wood object 26, such as its width 82, length 84 or height 86 (FIG. 3). Moreover, skilled persons will appreciate that FIG. 6 depicts a wood object 26 having a width 82 that is sufficiently narrow to fit within a single detection array unit 54. Wood objects 26 typically have a greater width 82 than a typical detection array unit, so several detection array units 54 may be placed side-by-side to span the entire width 82 or other dimension of the wood object 26.

In some embodiments, the lasers 44 are spaced sufficiently close to each other to satisfy a minimum density distribution that will provide sufficient illuminated target points on the surface of the wood object 26 to accurately characterize the surface grain angles. Skilled persons will appreciate that the optimal or maximum spacing between lasers 44 may be influenced by several laser parameters, including at least one of the laser energy, wavelength, spot size, distances of the lasers from the target, and their angles of incidence with respect to the surface of the wood object, as well as considerations concerning the packaging density of the lasers 44 devices.

In some exemplary embodiments, the lasers 44 are aligned in a row 80 and each has its own lens 72 to focus its energy onto the wood object 26 at approximately 5.1 cm (2 inches) from the laser 44. In such embodiments, the distance between each laser 44 may be less than 0.25 cm (0.1 inches). Skilled persons will appreciate, however, that the minimum distance between lasers 44 may be limited only by the physical size of each laser 44 and its packaging. Skilled persons will also appreciate that the distance between rows 80 of lasers 44 may be the same or different from the distance between lasers 44 in a row 80. Some preferred embodiments of a grain angle detection system 40 feature a dense line of individual lasers 44 that extends across the entire dimension of the wood object 26 in a direction transverse to the travel direction of the wood object 26 so that the entire surface 24 of the wood object 26 can be imaged.

Figure 7:
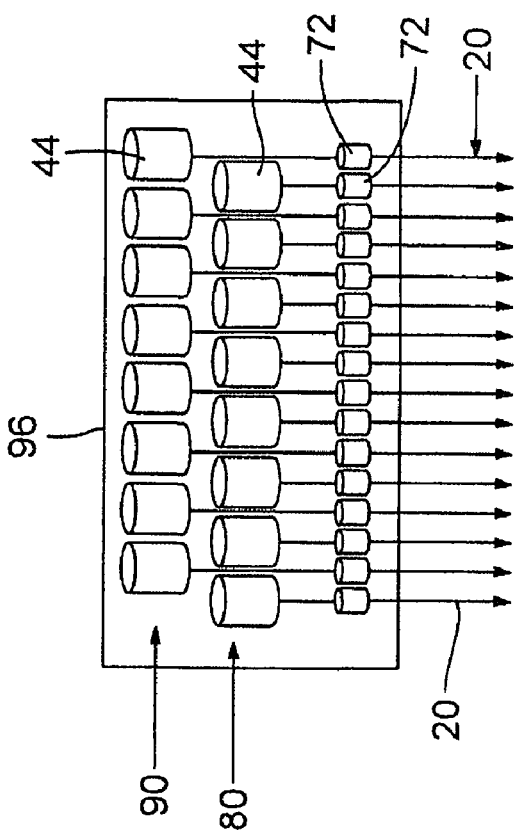
FIG. 7 is a side view of a portion of an exemplary improved grain angle detector demonstrating an exemplary arrangement of lasers and their lenses on a circuit board.

The electronics controlling the lasers 44 allow the lasers 44 to be individually controlled, such as individually turned on and off but other laser parameters may be individually controlled as well. In some embodiments, the lasers 44 are intended to have the same incidence angles and laser output parameters, including at least one of the laser energy, wavelength, spot size, repetition rate, pulse width, and distance of the laser from the target. Skilled persons will appreciate, however, that one or more lasers 44 may have different incidence angles and/or one or more other different laser output parameters. FIG. 7, for example, shows an exemplary arrangement in which groups 80 and 90 of lasers 44 are mounted on (soldered to) a circuit board 96 such that the groups 80 and 90 will be at different distances from the surface of the wood object 26. The lenses 72 for the lasers 44 of both groups 80 and 90 are, however, mounted in the same plane on the circuit board 96 in this example, but may provide different focal lengths so that the spot sizes resulting from each group of lasers 44 are intended to be the same. Skilled persons will appreciate that currently available single plane-mounted laser packages may influence the mounting density of the lasers 44. The exemplary embodiment shown in FIG. 7 would double the typical density by staggering the laser mounting at two levels. Skilled persons will also appreciate that in some embodiments the spot sizes from each group of lasers 44 or particular lasers 44 may be intentionally different. Thus, the lenses 72 may provide different focal lengths and may be mounted in the same or different planes.

With reference again to FIGS. 5 and 6, the individual lasers 44 and their respective detection fields 58 of the respective functional units 50 are labeled with letters A-H for convenience to describe exemplary operation of the grain angle detection system 40. The functional units 50 overlap such that the detection fields 58 generally include areas that cover the locations of the lasers 44 in adjacent functional units 50 and such that the detection fields 58 of adjacent lasers 44 share subsets of photosensor devices 52. For example in the exemplary embodiments depicted in FIGS. 5 and 6, the detection field 58A generally includes areas that cover the locations of lasers 44B, 44C, 44D, 44F, 44G, and 44H as well as laser 44A, and the detection field 58A also shares photosensor devices 52 that belong to detection fields 58B, 58C, 58D, 58E, 58F, 586, and 58H.

A high density of information can be handled in real-time by electronically sequencing the output from lasers 44 and multiplexing the photosensor devices 52 with corresponding functional units 50 so that the response detected for each laser 44 is separated from the response to other lasers 44. The lasers 44 may be turned on and off sequentially. The energy detected by the photosensor devices 52 surrounding the lasers 44 is sequentially measured in accordance with the laser activity to detect laser energy reflected from the surface of the wood object 26.

For example, FIG. 5 illustrates that for a brief time period all of the lasers 44A can be turned on and the response from their energy can be measured by the photosensor devices 52A (and photosensor devices 52AB) within the detection field 58A of functional unit 50A. (The photosensor devices 52 that are employed within both exemplary detection fields 58A and 58B are labeled as photosensor devices 52AB to emphasize the overlap of functional units 50A and 50B. For ease of description, however, the photosensor devices 52AB may be simply referred to as photosensor devices 52A or photosensor devices 52B to emphasize the associations with their respective functional units 50 and detection fields 58.) Skilled persons will appreciate that the detection field 58A preferably does not overlap another detection field 58A and that they are preferably spaced far enough apart so that the photosensor devices 52 from one detection field 58A are not affected by a laser 44A associated with a different detection field 58A.

In some embodiments, an exemplary time period might be in the range from 100 nanoseconds to 100 microseconds. In some embodiments, an exemplary time period might be in the range from 1 to 10 microseconds. A preferable time period may be influenced by one or more of the speed at which the wood object 26 travels through the detection field 58, the repetition rate of the lasers 44, the pulse width of the output of the lasers 44, the number of photosensor devices 52 in the detection field, the capabilities of the photosensor devices 52, or other factors known to skilled practitioners. In some embodiments, a wood object 26 may travel (with its major axis in the direction of travel 100 (lineally)) through a detection field 58 at speeds of about 91 to 1219 meters (300 to 4000 feet) per minute and more typically at speeds of at least 366 meters (1200 feet) per minute and less than about 610 meters (2000 feet) per minute. An exemplary time period may be accomplished by controlling or modulating the laser repetition rate or pulse width, or by controlling or modulating and intracavity or extracavity shutter, such as with an acousto-optic or electro-optic device, mechanical shutter, or other optical shutter device well known in the art.

During a subsequent time period all the lasers 44B can be activated and their corresponding photosensor devices 52B in detection fields 58B can be polled for their responses. In turn, each set of functional units 50 can be activated in a manner such that it is functionally isolated from the other sets of functional units 50. The control electronics can coordinate the timing of the power level and on/off sequencing of the lasers 44 and the photosensor devices 52 to eliminate "crosstalk" between opposing, overlapping, or adjacent units 50. In some embodiments, the responses from each functional unit 50 are recorded and analyzed separately.

In some embodiments, the photosensor devices 52 are configured to capture and transmit data that corresponds to a specific position on the wood object 26. If the wood object 26 is moving faster than the data can be collected by the photosensor devices 52, all the collected data is transmitted, and the system interpolates to fill in the holes so the processing software downstream doesn't see any difference.

In some embodiments, the response from the multiplexed photosensor devices 52A during the activation of the lasers 44A are converted from an analog to a digital value and combined with the information collected from photosensor devices 52B (or just the photosensor devices 52B that fall within detection field 58A) when the lasers 44B are activated. In some embodiments, the cumulative data may include data from all of the detection fields 58 that overlap a given detection field 58 (or just the photosensor devices 52 within them that overlap the given detection field 58). In some embodiments, the cumulative data may include data from only some of the detection fields 58 that overlap a given detection field 58. For example, in an embodiment where an array of functional units 50 is employed, the number of detection fields 58 analyzed with respect to a given detection field 58 may differ between those aligned in the direction of travel 100 and those aligned perpendicularly to the direction of travel 100. The combined data can be then used to analyze the wood surface fiber direction.

Another advantage of exemplary grain angle detection systems 40 are their ability to find the edges 110 of a wood object 26 if the wood object 26 object is narrower than the width of the row 80. There is often some play in wood conveying means that permits wood objects to wander a little in a direction transverse to the direction of travel. Knowledge of the edge 110 of the wood object 26 facilitates registry of the positions of the other surface data points. Such registry facilitates correlation of the dive angle data with other wood characteristic data such as for final use analysis or wood tracking such as described in detail in U.S. Pat. No. 7,200,458 of Carman et al., which is herein incorporated by reference.

When the activated lasers 44 lie over an area where the wood object 26 is absent, no energy is identified by the photosensor devices 52. The lack of response immediately next to a laser 44 that does elicit a response can be used to identify the position of the edge 110 of the wood object 26. FIG. 6 shows an example in which the outermost lasers 44A and 44B will produce a response when they are activated, the outermost laser 44D in the subset will miss the surface of the wood object 26 and thus produce no response from the surrounding photosensor devices 52, and only a portion of the laser spot of the outermost laser 44C may impinge the surface 24 of the wood object 26. The reflected energy detected by the photosensor devices 52 in the detection field associated with the outermost laser 44C will indicate the degree to which the laser spot of the outermost laser 44c impinged the surface 24 of the wood object 26.

In a typical application, a wood object 26, such as a board, is sent lineally through the grain angle detection system 40, and the position of the wood object 26 is tracked. The energy detected by the photosensor devices 52 is captured by sensor electronics and exported off the sensor to an external computer system. (Alternatively, the data can be preprocessed by the electronics.) The coordinates where the data is collected along the surface of the wood object 26 are also recorded in order to properly reference the data to the surface of the moving wood object 26. Two vectors can be calculated from the data using the centers of highest energy density and the geometric position of the photosensor devices 52 with respect to the active laser 44. The direction of each vector is used to generate values for both surface angle and dive angle for each laser spot. Similar analyses are disclosed in U.S. Pat. No. 4,606,645 Matthews, which is herein incorporated by reference. Skilled persons will appreciate that while calculations and analysis may be based on reflections from a cylindrical shape as described by Matthews, calculations or analysis may also be modified to address the reality that much of the reflections are coming from sliced open cells or a combination of whole and sliced open cells.

Typical uses of grain angle data include identifying areas of a wood object 26 where the grain angle might vary more than a specified maximum amount. Moreover, grain angle information can be used to help detect, size, and classify defects. For example, a grain angle found to be in excess of one inch (2.54 cm) in the width distance over six inches (15.2 cm) of length distance can be identified as a "Slope of Grain of 1 in 6" (about 10 degrees) and is an indicator of reduced board strength. This information can be used in the decision process for further manufacturing of the wood object 26 and/or specifying a final grade for it.

Another use of grain angle data would be to combine the grain angle information with data from other sensors to support identification, classification, and measurement of wood fiber characteristics, such as defects. For example, some knots can blend but grain angles deviations tend to be very apparent. So, an indication that the grain is diving and/or angled radically in the surface plane near an area that might "look" like a knot can help a lumber scanning system make a better decision on how to characterize or process that area of the wood object 26. For example, in cases where short pieces of wood are destined for applications with finger joints, grain angle information can be used to avoid cuts where finger joints would be likely to pull out.

Whether for purposes of dive angle detection or edge detection, the information from the photosensor devices 52 can be collected and processed to identify the direction and dive angle of the tracheid cells 22 and used for grading and determination of the end use of portions of the wood object 26. The information obtained from photosensors 52 may be compressed locally and transmitted to other equipment to be analyzed externally for relevant wood fiber characteristics.

The grain angle detection system 40 may be implemented in a single electro-optical assembly that may comprise an enclosure housing for an electronic control board connected to circuit cards that contain the lasers 44 and photosensor devices 52. The enclosure housing is preferably adapted to protect the system components from adverse ambient temperature, debris, vibration, and humidity. In some embodiments, the photosensor devices 52, the detection array unit 54, and/or the enclosure housing for the grain angle detection system. 40 can be positioned within about 2.54 cm (one inch) from the surface of the wood object 26. In some embodiments, the entire assembly of detection array unit(s) and or the enclosure housing may have a width 112 of as little as 3.8-5.1 cm (1.5-2 inches). The very small footprint of the grain angle detection system 40 facilitates optional implementation and positioning of multiple photosensor arrays around both surfaces and sides of the wood object 26.

The photosensors 52 may be soldered onto their own card or circuit board 96. These circuit boards 96 can be plugged into connectors that are provided on an electronics control board that may be protected by the enclosure housing. The control board may include processing and communication hardware. The electronics control board may control the lasers 44 and photosensors 52, may preprocess the resulting sensor information, and may transmit the results to an external computer system via an Ethernet connection. A second Ethernet connection may provide external synchronization control signals to some or all of the components of the grain angle detection system 40. A third Ethernet connection may provide a means of diagnostic control signals and remote programming of the system components.

An alternative embodiment could have the lasers 44 and photosensor devices 52 soldered to the same circuit board 96. An alternative embodiment could have the lasers 44 and/or photosensors 52 soldered directly onto an electronic control board. An alternative embodiment could have the lasers 44 and/or photosensors 52 plugged into sockets instead of soldering them to a circuit board 96. Some alternative embodiments could use a different parallel or serial communication method between system components and the external computer system besides Ethernet connections. An alternative embodiment could utilize a different communication method for synchronization control signals, diagnostic control signals, and remote programming of the system components. An alternative embodiment could be configured to not require external control of diagnostics or remote programming capability. An alternative embodiment could be configured to operate without external synchronous control signals. Such exemplary embodiments might then transmit information that is collected at a fixed rate. One or more alternative forms of photosensor devices 52 could be configured to locally analyze a part or all of the data collected by the electronics. An alternative form of the photosensors 52 could work without compressing the data before transmitting it externally.

Preferred image processing techniques as previously described can be used on one or more faces 36, sides 38, and/or ends 42 of surfaced or unsurfaced wood objects 26 of any moisture content, such as green (uncured) or dry wood, The grain angle detection system 40 can be installed in an enclosure that can be mounted to analyze one surface 24 of a wood object 26. Alternatively, multiple enclosures containing separate grain angle detection systems 40 can be installed in various orientations and positions and synchronized externally (to minimize possible crosstalk between detection fields) in order to analyze multiple surfaces 24 of the wood object 26. Alternative full or partial wraparound embodiments (perhaps in single enclosure) could support the analysis of multiple surfaces 24 of a wood object 26. An alternative embodiment could employ separated grain angle detection systems 40 in multiple locations or enclosures to support the analysis of multiple areas of the same face 36 of a wood object 26, or the grain angle detection systems 40 can be positioned to examine different surfaces 24 of the wood object 26. For example, an alternative form of grain angle detection system 40 could employ multiple units positioned on different sides of a wood object displaced along the length of the wood object so that they do not introduce crosstalk between them. Alternative embodiments of grain angle detection systems 40 could be comprised of a single unit that contains lasers 44 and photosensors 52 positioned in different planes in order to analyze multiple surface areas of the same wood object 26. An alternative form of the grain angle detection system 40 could employ larger photosensor devices 52 to reduce the number of detectors 52. An alternative embodiment may impinge the wood object with different polarizations of light from adjacent light sources and independently or collectively controlled polarizations filters or wavelength selective filters may be employed with the photosensors 52 such that the detection fields 58 of adjacent lasers 44 detect different polarizations or different wavelengths.

Figure 8:
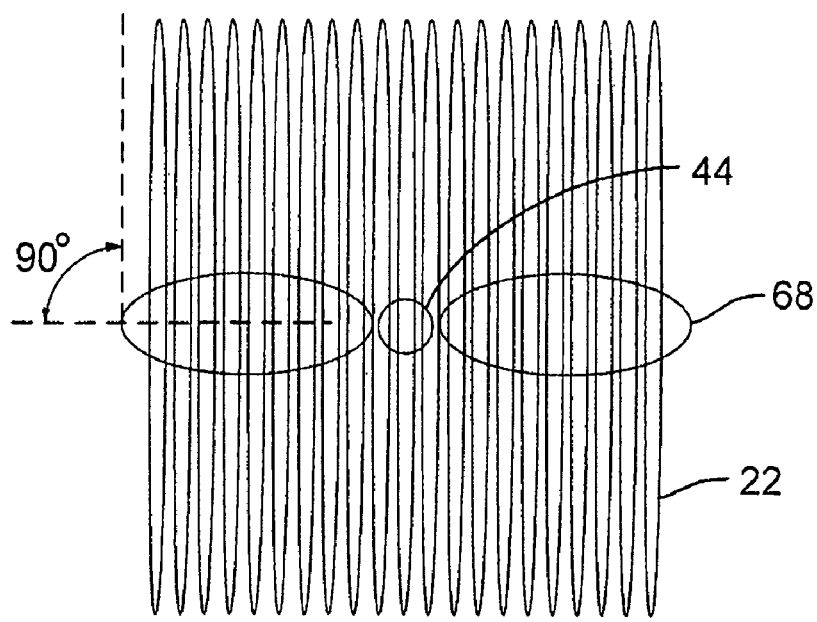
FIG. 8 is a top view illustrating energy reflected from the surface of a tracheid cell having no dive angle.

FIG. 8 is a top view illustrating energy reflected from the surface of a tracheid cell 22 having no dive angle. As previously, discussed, the largest quantity of reflected energy 68 is observed at a 45 degree angle with respect to the angle of incidence, and 90 degrees from the direction of the long axis of the tracheid cell 22 when there is no dive angle. A dive angle is present when the tracheid cells 22 align in a direction not parallel with the surface 24 plane of the wood object 26.

Figure 9:
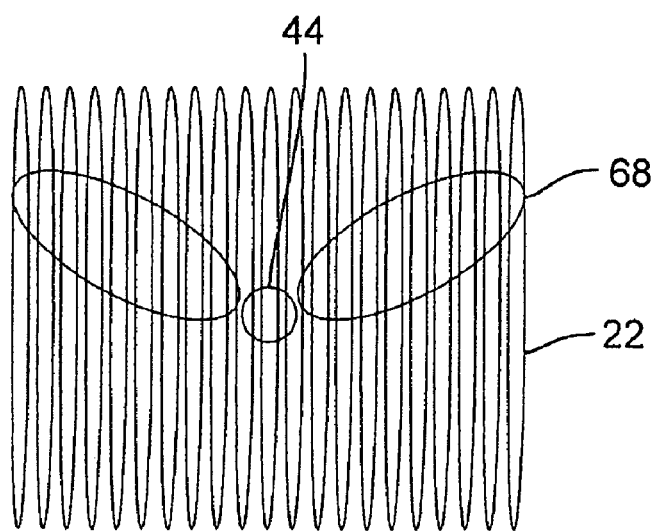
FIG. 9 is a top view illustrating energy reflected from the surface of a diving tracheid cell.
Figure 10:
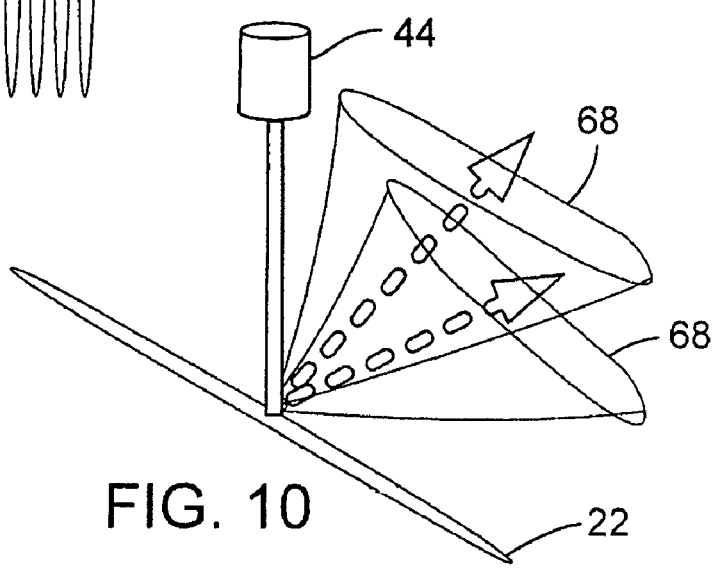
FIG. 10 is a perspective view of energy reflected from the surface of a diving tracheid cell.

FIG. 9 is a top view illustrating energy reflected from the surface 24 of a diving tracheid cell 22, and FIG. 10 is a perspective view of energy reflected from the surface 24 of a diving tracheid cell 22. A dive angle is detected because the direction of the reflected energy 68 varies with the angle of incidence, as shown in the top view in FIG. 9 and the perspective view in FIG. 10.

The energy from an individual laser 44 typically generates a response from the surface 24 of the wood object 26 that is most prevalent within a concentric circle around the laser axis and peaks at a 45 degree angle from where the laser strikes the surface 24. When multiple lasers 44 are arranged to provide a dense coverage of the surface 24, their combined response can be observed in the response from photosensors 52 arranged in overlapping concentric circles. Most of the energy reflected from an individual laser 44 can be detected within a concentric circle around the laser 44. In some embodiments, the radius of the circle may be dependent upon the distance of the photosensors 52 from the wood surface 24.

Skilled persons will appreciate that the relative movement between the wood object 26 and components of the grain angle detection system 40 determines the distance and angle from the wood surface 24, which can influence the angles detected and affect the results obtained. In most cases, movement effects are not significant but can be addressed by controlling the timing of the lasers 44 and photosensors 52 and/or by appropriate weighting to address the speed of travel. However, in circumstances where extreme precision is desired, triangulation sensors can be added to determine the actual distance the photosensors 52 are from the wood surface 24 when data is collected. The distance data can be used to mathematically compensate for angle inaccuracies in the data colleted by photosensors 52.

The techniques disclosed herein are easily sufficient for any current and foreseeable scanning applications that would benefit from a very accurate map of fiber direction.

With respect to the above description, skilled persons will appreciate that dimensional relationships, materials, shape, form, function, assembly, and manner of operation of system components will vary, to include variations in size and specific applications. It will be obvious to those having skill in the art that many changes may be made to the details of the above-described embodiments of the invention without departing from the underlying principles thereof. The scope of the present invention should, therefore, be determined only by the following claims.

The invention claimed is:

1. A grain angle detection system, comprising:
    a row of light sources for generating respective beams of light that impinge respective spot areas on a surface of a wood object;
    an array of light sensors adapted to detect light reflected from the surface of the wood object in response to impingement by the spot areas, the array including multiple sets of light sensors in which each set of light sensors is sensitive to reflections from a respective spot area formed by a respective light source, the sets of light sensors overlapping such that each set includes light sensors that belong to at least two other sets;
    a controller for causing temporally-spaced activation of the light sources in a manner that permits overlapping sets of light sensors to obtain reflection data independently for each spot area generated by a respective light source; and
    data processing software for determining at least one of grain direction or dive angle at the wood surface illuminated by the light sources.

2. The grain angle detection system of claim 1 in which at least two light sources are activated simultaneously.

3. The grain angle detection system of claim 2 in which the at least two light sources have respective nonoverlapping sets of light sensors.

4. The grain angle detection system of claim 1 in which at least one of the light sources comprises a laser.

5. The grain angle detection system of claim 1 in which at least one of the light sources comprises a diode laser or a fiber laser.

6. The grain angle detection system of claim 1 in which the light sources emit light comprising the same wavelength.

7. The grain angle detection system of claim 1 in which at least two of the light sources emit light comprising different wavelengths.

8. The grain angle detection system of claim 1 in which at least two of the light sources emit light comprising the same repetition rate, same pulsewidth, or both.

9. The grain angle detection system of claim 1 in which at least two of the light sources emit light at different repetition rates, different pulse widths, or both.

10. The grain angle detection system of claim 1 in which at least two of the light sources emit light at the same incidence angle on the wood object.

11. The grain angle detection system of claim 1 in which at least two of the light sources emit light at different incidence angles on the wood object.

12. The grain angle detection system of claim 1 in which at least two of the light sources provide light of different polarizations to the wood object.

13. The grain angle detection system of claim 1 in which the light sources form a row.

14. The grain angle detection system of claim 1 in which the light sources form at least two rows.

15. The grain angle detection system of claim 14 in which at least two rows are mounted at the same distance from the wood surface.

16. The grain angle detection system of claim 14 in which at least two rows are mounted at different distances from the wood surface.

17. The grain angle detection system of claim 16 in which at least two rows are mounted generally in a plane transverse to the wood surface and the lasers in the different rows employ lens elements with different focal properties.

18. The grain angle detection system of claim 1 in which the light source has a spot size on the wood surface that is larger than the diameter of a tracheid cell.

19. The grain angle detection system of claim 1 in which the light source has a spot size on the wood surface that is larger than the additive diameters of multiple tracheid cells.

20. A method of determining grain characteristics of a piece of wood, comprising:
    selectively illuminating multiple discrete spot areas on a wood surface;

detecting light reflected from respective discrete spot areas with respective sets of sensors wherein each set of light sensors is sensitive to reflections from a respective spot area and wherein each set of light sensors includes light sensors that belong to at least two other sets of light sensors; and controlling selective simultaneous illumination of multiple spot areas to obtain reflection data with respective sets of simultaneously activated light sensors for each of the spot areas illuminated simultaneously such that the sets of sensors simultaneously illuminated are nonoverlapping.

21. The method of claim 20 wherein the spot areas illuminated simultaneously are nonoverlapping.

22. The method of claim 20 in which the light sensors that belong to at least two other sets of light sensors are reactivated at temporally-spaced time intervals when the two other sets of light sensors are activated with their respective spot areas.

23. The method of claim 20 in which at least one of the spot areas is provided by a laser.

24. The method of claim 23 in which the laser comprises a diode laser or a fiber laser.

25. The method of claim 20 in which the spot areas are provided by light sources that emit light comprising the same wavelength.

26. The method of claim 20 in which the spot areas are provided by at least two light sources that emit light comprising different wavelengths.

27. The method of claim 20 in which the spot areas are provided to the wood surface for equal amounts of time.

28. The method of claim 20 in which the spot areas are provided by at least two light sources that emit light at the same incidence angle on the wood surface.

29. The method of claim 20 in which the spot areas are provided by at least two light sources that emit light at different incidence angles on the wood surface.

30. The method of claim 20 in which at least two of the light sources provide light of different polarizations to the wood object.

31. The method of claim 20 in which the spot areas simultaneously illuminated form a row.

32. The method of claim 20 in which the spot areas on the wood surface are respectively larger than the diameter of a tracheid cell.

33. The method of claim 20 in which the spot areas of the wood surface are respectively larger than the additive diameters of multiple tracheid cells.

* * * * *